(12) United States Patent
Campbell et al.

(10) Patent No.: US 7,786,312 B2
(45) Date of Patent: Aug. 31, 2010

(54) METHODS OF PREPARING HETEROCYCLIC BORONIC ACIDS AND DERIVATIVES THEREOF

(75) Inventors: David Alan Campbell, San Diego, CA (US); David T. Winn, San Diego, CA (US)

(73) Assignee: Phenomix Corporation, San Diego, CA (US)

( * ) Notice: Subject to any disclaimer, the term of this patent is extended or adjusted under 35 U.S.C. 154(b) by 0 days.

(21) Appl. No.: 11/996,792

(22) PCT Filed: Jul. 27, 2006

(86) PCT No.: PCT/US2006/029451

§ 371 (c)(1),
(2), (4) Date: Jun. 17, 2008

(87) PCT Pub. No.: WO2007/016356

PCT Pub. Date: Feb. 8, 2007

(65) Prior Publication Data

US 2008/0300413 A1 Dec. 4, 2008

Related U.S. Application Data

(60) Provisional application No. 60/704,380, filed on Aug. 1, 2005.

(51) Int. Cl.
*C07F 5/02* (2006.01)
(52) U.S. Cl. .................................. 548/408; 548/558
(58) Field of Classification Search ................ 548/405, 548/558
See application file for complete search history.

(56) References Cited

U.S. PATENT DOCUMENTS

| 7,399,869 B2 * | 7/2008 | Cohen et al. ............... 548/405 |
| 2006/0258621 A1 | 11/2006 | Campbell et al. |
| 2006/0264400 A1 | 11/2006 | Campbell et al. |

FOREIGN PATENT DOCUMENTS

| WO | WO-2005047297 A1 | 5/2005 |
| WO | WO-2007016356 A1 | 2/2007 |
| WO | WO-2008109681 A2 | 9/2008 |
| WO | WO-2008109681 A3 | 9/2008 |

OTHER PUBLICATIONS

Coutts et al. (J. Med. Chem. 1996, 39, 2087-2094).*
Peretto et al. (Chem. Commun., 2003, 2312-2313).*
Wang et al. (J. Phys. Chem. B 2001, 105, 3295-3299).*
"International Application Serial No. PCT/US06/29451, International Search Report mailed Dec. 15, 2006", 4 pgs.
"International Application Serial No. PCT/US06/29451, Written Opinion mailed Dec. 15, 2006", 3 pgs.
"International Application Serial No. PCT/US2008/055927, International Search Report mailed Sep. 10, 2008", 5 pgs.
"International Application Serial No. PCT/US2008/055927, Written Opinion mailed Sep. 10, 2008", 6 pgs.
"U.S. Appl. No. 12/529,016, Preliminary Amendment mailed Aug. 27, 2009", 15 pgs.
"Chinese Application Serial No. 200680028192.0, Office action mailed Jan. 15, 2010", 3 pgs.

* cited by examiner

*Primary Examiner*—Kamal A Saeed
*Assistant Examiner*—Valerie Rodriguez-Garcia
(74) *Attorney, Agent, or Firm*—Schwegman, Lundberg & Woessner, P.A.

(57) ABSTRACT

In the context of synthesizing heterocyclic boronic acid compounds, a convergent synthetic methodology is particularly efficient for preparing boropyrrolidines and derivatives of boropyrrolidines.

41 Claims, No Drawings

METHODS OF PREPARING HETEROCYCLIC BORONIC ACIDS AND DERIVATIVES THEREOF

RELATED APPLICATIONS

This application is a U.S. National-Stage entry under 35 U.S.C. §371 based on International Application No. PCT/US2006/029451, filed Jul. 27, 2006 and published in English as WO 2007/016356 on Feb. 8, 2007, which designates the United States of America, and claims priority to U.S. Provisional Application Ser. No. 60/704,380, filed Aug. 1, 2005, which are incorporated herein by reference in their entirety.

FIELD OF THE INVENTION

The present invention relates generally to synthetic methods for preparing heterocyclic boronic acids and derivatives thereof. More specifically, the invention relates to synthetic methods for preparing boropyrrolidine acids and esters.

BACKGROUND OF THE INVENTION

Dipeptidyl peptidase-IV (DPP-IV) is a serine protease that belongs to a group of post-proline/alanine cleaving amino-dipeptidases. DPP-IV catalyzes the release of an N-terminal dipeptide preferentially from proteins with N-terminal penultimate proline or alanine. In vivo administration of synthetic inhibitors of DPP-IV have been shown to improve glycemic control and therefore, such inhibitors have been proposed for the treatment of patients with type II diabetes and related conditions.

Recently, heterocyclic boronic acid inhibitors selective for DPP-IV over DPP-VIII and other related enzymes have been disclosed. In addition, pharmaceutical compositions including such compounds and methods for the use of such compounds are described. Although these applications disclose various methods for the synthesis of heterocylic boronic acid inhibitors, new methods which produce these compounds with improved purity and yield are desirable because of their increasing importance in pharmaceutical formulations and methods of treatment for diabetes and related diseases.

SUMMARY OF THE INVENTION

The present invention provides efficient methods for synthesizing heterocyclic boronic acid compounds. Specifically, convergent synthetic methods for preparing pyrrolidine boronic acids and derivatives thereof are provided. Such compounds are useful, for example, in treating patients suffering from diabetes and related diseases. Briefly, the method is directed to the coupling of an active carbonyl compound of Formula I given below with an amino compound of Formula II given below. Appropriate amine and boronic acid protecting groups are employed to circumvent undesirable side reactions with these groups. The active carbonyl compound may be any carboxylic acid derivative capable of forming an amide bond with an amine. Such active carbonyl compounds include but are not limited to acid chlorides, mixed anhydrides, activated esters, azides and the like, as well as the intermediates formed by combination of the carboxylic acid with a coupling agent such as a diimide and the like.

DETAILED DESCRIPTION OF THE INVENTION

The present invention provides methods for synthesizing N-substituted amino acetyl pyrrolidine boronic acids and derivatives thereof. Accordingly, in one aspect, there are provided methods which include coupling a compound of Formula I

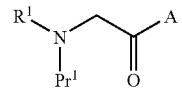

with a compound of Formula II

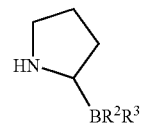

to provide a compound of Formula III

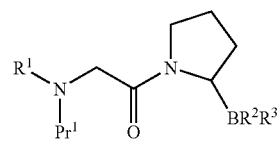

wherein,

A is OH or a group which may be displaced by an amine;

$Pr^1$ is an N-protecting group;

$R^1$ is a substituted or unsubstituted hydrocarbon group optionally containing hetero atoms as defined herein; preferably, $R^1$ is a substituted or unsubstituted alkyl, alkenyl, alkynyl, cycloalkyl, cycloalkylalkyl, cycloalkenyl, cycloalkenylalkyl, aryl, arylalkyl, heterocyclyl, heterocyclylalkyl, heteroaryl, or heteroarylalkyl group; and $R^2$ and $R^3$ are independently or together a group that can be hydrolyzed to hydroxyl. The 2-pyrrolidine boronic acid can be readily synthesized using methods described in the literature.

In another aspect of the present invention, there are provided methods of preparing the compound of Formula I by alkylating a compound of Formula IV, $R^1$—$NH_2$, in the presence of base with a compound of Formula V, L-$CH_2$—COOR', wherein L is a leaving group that is stable as a negatively charged group or as a group that is ionizable to form a negatively charged group, $R^1$ is as previously defined, and R' is a carboxyl-protecting group;

to provide a compound of Formula VI, $R^1$—NH—$CH_2$—COOR', protecting the secondary amine to provide a compound of Formula VII, $R^1$—N($Pr^1$)—$CH_2$—COOR', and converting a compound of Formula VII to a compound of Formula I. In this aspect, the amine $R^1$—$NH_2$ is available also from commercial sources such as Sigma Aldrich and also can be readily synthesized by routine methods known to those of skill in the art. See for example "Advanced Organic Chemistry" 4th Ed., J. March, Wiley Interscience, New York, N.Y. 1992 for directions for synthesis of such amines.

In some such embodiments, L is Cl, Br, I, mesylate, or triflate. In other such embodiments, the base is sodium carbonate, potassium carbonate, or cesium carbonate.

As indicated above, R' is a carboxyl protecting group such as a substituted or unsubstituted alkyl, alkenyl, or aralkyl group. Thus R' can be methyl, ethyl, t-butyl, allyl, or benzyl. Thus, in some embodiments, the compound of Formula VII is hydrolyzed with base to the compound of Formula I wherein A is OH.

In other embodiments, $Pr^1$ is, e.g. Cbz or Boc. Thus, in some embodiments, the protection of the secondary amine of Formula VI is carried out with a substituted or unsubstituted alkoxychloroformate or aryloxychloroformate. This protection step with the amine protecting group $Pr^1$ is especially advantageous for the process of the present invention because it enables the facile separation of the desired down stream products from the corresponding side products of the reaction sequence. Under other processing procedures, these side product separations are difficult to achieve.

In some embodiments of the methods disclosed herein, A is OH and Formula I is therefore a carboxylic acid. As such, the coupling of the compound of Formula I to the compound of Formula II is conducted using a coupling reagent. Any coupling reagent suitable for forming an amide bond with a secondary amine may be used for this reaction. Suitable coupling reagents include DCC, DIC, EDCI, HATU, BOP, BOP—Cl, PyBOP, PyBrOP, and the like. The coupling may be conducted in the presence of a coupling additive that facilitates the reaction such as, but not limited to HOBt, HOAt, or DMAP. It is well within the skill of the ordinary artisan to select an appropriate combination of coupling reagent and coupling additive for the task at hand.

The coupling may be conducted in the presence of a base, where, for example, the compound of Formula II is employed as a salt such as an HCl salt. Any base which does not interfere with the coupling may be used such as triethylamine, diisopropylethylamine, or N-methylmorpholine. The amount of base used will depend on the amount of salt to be neutralized and whether the coupling reagent, the coupling additive, or byproducts from the reaction of the coupling reagent and/or additive must be neutralized to facilitate the coupling reaction. It is well within the skill of the ordinary artisan to select the amount and type of base necessary for the coupling reaction.

In another embodiment of the present methods, A is a group which may be displaced by an amine. Such groups are well known in the art and include, for example, imidazolyl, F, Cl, Br, I, azide, pentafluorophenoxy, p-nitrophenoxy, N-oxysuccinimide, or OC(O)OR, wherein R is substituted or unsubstituted $C_{1-8}$ alkyl. Thus, A, in combination with the carbonyl to which it is attached, forms acid halides, active esters, mixed anhydrides, and other activated acyl groups. A base such as described above may be used, where necessary, to neutralize salts of the compound of Formula II, and/or any acid byproducts of the displacement reaction.

In some embodiments of the methods in which A is a group which may be displaced by an amine, A is formed from the corresponding acid and then reacted with the compound of Formula II in a one-pot reaction. For example, the acid of Formula I (i.e. A is OH) may be converted to the mixed anhydride (A is OC(O)OR) by reaction with an alkylchloroformate (e.g., isobutylchloroformate or t-butylchloroformate) in the presence of base. Typically, the formation of the mixed anhydride is carried out at a temperature below room temperature such as from about 0° C. to about −15° C. or less. After a short period of time, the compound of Formula II or a salt thereof is added to the mixed anhydride to form the compound of Formula III. If Formula II is in the form of an acid addition salt, a sufficient amount of more base must be added to neutralize the acid, such as 1.1, 1.2, 1.5, 2 or more equivalents.

In some embodiments of the present methods, $R^1$ is a) $(C_{1-12})$alkyl; $(C_{2-12})$alkenyl; $(C_{2-2})$alkynyl; $(C_{3-12})$cycloalkyl; or $(C_{3-12})$cycloalkenyl; where the alkyl, alkenyl, alkynyl, cycloalkyl and cycloalkenyl groups are optionally mono- or independently plurisubstituted with $R^6$, and where the alkyl, alkenyl, alkynyl portions include linear or branched chains and may include cyclic portions;

$R^6$ is $(C_{1-6})$alkyl; $(C_{1-6})$alkoxy; cycloalkyl; carboxy; acetamido; cyano; nitro; halogen; hydroxy; hydroxy $(C_{1-6})$alkyl; hydroxymethyl; trifluoromethyl; trifluoromethoxy; sulfamoyl; sulfonamido; carbamoyl; aryl; heteroaryl; where the aryl and heteroaryl groups are optionally mono- or independently plurisubstituted with $R^7$; amino, where the amino group is optionally mono- or independently plurisubstituted with $R^8$; —$SOR^8$; —$SO_2R^8$; —$COR^8$; —$CO_2R^8$, —$CONHR^8$; —$CON(R^8)_2$; —$OR^8$; or —S—$R^8$;

$R^7$ is halogen; $(C_{1-10})$alkyl; $(C_{1-10})$alkoxy; $(C_{1-10})$alkylamino; $(C_{1-10})$ dialkylamino; benzyl; benzyloxy; hydroxyl$(C_{1-6})$alkyl; hydroxymethyl; nitro; trifluoromethyl; trifluoromethoxy; trifluoromethylthio; N-hydroxyimino; cyano; carboxy; acetamido; hydroxy; sulfamoyl; sulfonamido; or carbamoyl;

$R^8$ is $(C_{1-10})$alkyl; $(C_{2-10})$alkenyl; $(C_{2-10})$alkynyl; $(C_{3-10})$cycloalkyl; $(C_{5-10})$cycloalkenyl; benzyl; phenethyl; aryl; or heteroaryl; where the alkyl, alkenyl, alkynyl, cycloalkyl, cycloalkenyl groups are optionally mono- or independently plurisubstituted with aryl or heteroaryl where the aryl and heteroaryl groups are optionally mono- or independently plurisubstituted with $R^7$; and where the aryl and heteroaryl groups are optionally mono- or independently plurisubstituted with $R^7$;

b) aryl optionally fused to a $(C_{3-10})$cycloalkyl; or heteroaryl optionally fused to a $(C_{3-10})$cycloalkyl; where the aryl and heteroaryl groups are optionally mono- or independently plurisubstituted with $R^7$;

c) indanyl; 1,2,3,4-tetrahydronaphthyl; $(CH_2)_j$adamantyl in which j is 0-3; or a [2.2.1] or [3.1.1] bicyclic carbocyclic moiety, including (4-pentylbicyclo[2.2.2]oct-1-yl) amine; where the indanyl, 1,2,3,4-tetrahydronaphthyl, $(CH_2)_j$adamantyl, and [2.2.1] or [3.1.1] bicyclic carbocyclic moieties are optionally mono- or independently plurisubstituted with hydroxy, $(C_{1-8})$alkyl, $(C_{1-8})$alkoxy, $(C_{1-8})$alkanoyloxy, or $R^9R^{10}N$—CO—O—, where $R^9$ and $R^{10}$ are independently $(C_{1-8})$alkyl, or phenyl, where the alkyl and phenyl groups are optionally mono- or independently plurisubstituted with $(C_{1-8})$alkyl, $(C_{1-8})$alkoxy, halogen, or trifluoromethyl, or $R^9$ and $R^{10}$ together are $(C_{3-6})$alkylene;

d) $R^{11}(CH_2)_p$— where $R^{11}$ is 2-oxopyrrolidinyl; $(C_{1-6})$alkoxy; phenyl; phenoxy; $(C_{1-8})$cycloalkyl; [3.3.3] bicyclic carbocyclic moiety; pyridinyl; naphthyl; cyclohexenyl; or adamantyl; where the 2-oxopyrrolidinyl, $(C_{1-6})$alkoxy, phenyl, pyridinyl, and naphthyl groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono- or independently plurisubstituted with $(C_{1-8})$alkyl; and p is 0 to 3;

$R^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsulfonyl; phenylsulfonyl; aryl; heteroaryl; where the aryl and heteroaryl groups are optionally mono- or independently plurisubstituted with $R^7$;

e) $(R^{13})_2CH(CH_2)_q$—, where $R^{13}$ is phenyl; in which the phenyl groups are independently optionally mono- or independently disubstituted with $R^{12}$; and q is 0 to 3;

f) a group of the formula:

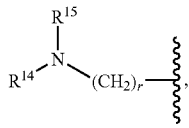

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and r is 2 to 6;

g) a group of the formula:

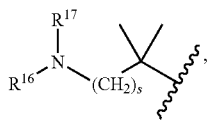

where $R^{16}$ and $R^{17}$ are each independently hydrogen; $(C_{1-8})$alkyl; $(C_{1-6})$alkylcarbonyl; di-$(C_{1-6})$alkylaminocarbonyl; benzyl; benzoyl; pyridine; pyrimidine; phenyl; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{16}$ and $R^{17}$ together form a $(C_{3-12})$cycloalkyl ring; and s is 1 to 6;

h) a group of the formula:

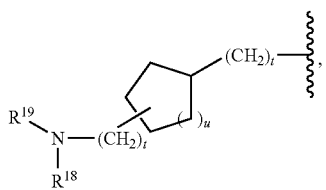

where $R^{18}$ and $R^{19}$ are independently hydrogen; $(C_{1-8})$alkyl; $(C_{1-6})$alkylcarbonyl; di-$(C_{1-6})$alkylaminocarbonyl; benzyl; benzothiazole; benzoyl; pyridine; pyrimidine; phenyl; phenylaminocarbonyl; alkylsulfonyl; or phenylsulfonyl; where the benzyl, benzoyl, benzothiazole, pyridine, pyrimidine, phenyl, phenylaminocarbonyl, alkylsulfonyl, and phenylsulfonyl groups are optionally mono- or independently di-substituted with $R^{12}$; or $R^{18}$ and $R^{19}$ together form a $(C_{3-12})$cycloalkyl ring; each t is independently 0 to 6; and u is 0 to 3;

i) a group of the formula:

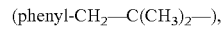

(phenyl-CH$_2$—C(CH$_3$)$_2$—), where the phenyl group is optionally mono- or independently plurisubstituted with $R^{12}$;

j) a group of the formula:

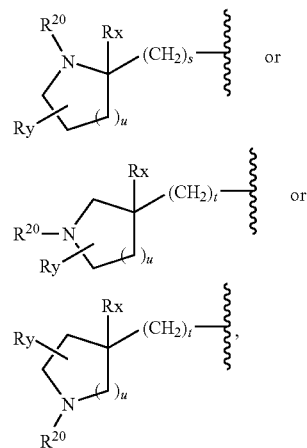

where $R^{20}$ is an N-protecting group or is $(C_{1-8})$alkyl; $(C_{1-6})$alkylcarbonyl; di-$(C_{1-6})$alkylaminocarbonyl; $(C_{3-8})$cycloalkylcarbonyl; benzyl; benzoyl; $(C_{1-6})$alkyloxycarbonyl; aralkyloxycarbonyl, pyridine; pyrimidine; phenyl; phenyl substituted thiazole ring; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; $R_x$ is hydrogen; alkyl; cycloalkyl; alkenyl, cycloalkylalkyl, aryl, aralkyl, heterocyclyl, or heterocyclylalkyl, each optionally mono- or independently di-substituted with $R^{12}$; $R_y$ is absent or is halogen, $(C_{1-8})$alkyl, $(C_{1-8})$alkoxy, O-alkylcarboxylate, O-aralkylcarboxylate, N-alkylcarboxamido, N-aralkylcarboxamido; or phenyl;
s is 1 to 6; t is 0 to 6; and u is 0 to 3; or k) a group of the formula:

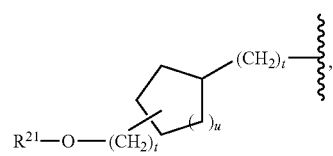

where $R^{21}$ is hydrogen; $(C_{1-8})$alkyl; benzyl; or phenyl; in which the benzyl and phenyl groups are optionally mono- or independently di-substituted on the ring with $R^{12}$; each t is independently 0 to 6; and u is 0 to 3;

l) alkyl; alkenyl; alkynyl; cycloalkyl; cycloalkylalkyl; bicycloalkyl; tricycloalkyl; alkylcycloalkyl; hydroxyalkyl; hydroxyalkylcycloalkyl; hydroxycycloalkyl; hydroxybicycloalkyl; hydroxytricycloalkyl; bicycloalkylalkyl; alkylbicycloalkyl; alkylthioalkyl; arylalkylthioalkyl; cycloalkenyl; aryl, aralkyl; heteroaryl; heteroarylalkyl; cycloheteroalkyl or cycloheteroalkylalkyl; all optionally mono- or independently plurisubstituted with halogen, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylamino-carbonyl, alkylaminocarbonyl, alkenylaminocarbonyl, alkylcarbonyloxy, alkylcarbonylamino, arylcarbonylamino, alkylsulfonylamino, alkylaminocarbonyl-amino, alkoxycarbonylamino, alkylsulfonyl, aminosulfinyl, aminosulfonyl, alkylsulfinyl, sulfonamido or sulfonyl.

In some such embodiments of the present methods, $R^1$ is a) aryl optionally fused to heteroaryl optionally fused to a $(C_{3-10})$cycloalkyl; where the aryl and heteroaryl groups are optionally mono- or independently plurisubstituted with $R^7$;

$R^7$ is halogen; $(C_{1-10})$alkyl; $(C_{1-10})$alkoxy; $(C_{1-10})$alkylamino; $(C_{1-10})$ dialkylamino; benzyl; benzyloxy; hydroxyl$(C_{1-6})$alkyl; hydroxymethyl; nitro; trifluoromethyl; trifluoromethoxy; trifluoromethylthio; N-hydroxyimino; cyano; carboxy; acetamido; hydroxy; sulfamoyl; sulfonamido; or carbamoyl;

b) $R^{11}$ $(CH_2)_p$— where $R^{11}$ is 2-oxopyrrolidinyl; $(C_{1-6})$alkoxy; phenyl; phenoxy; $(C_{1-8})$cycloalkyl; [3.3.3] bicyclic carbocyclic moiety; pyridinyl; naphthyl; cyclohexenyl; or adamantyl; where the 2-oxopyrrolidinyl, $(C_{1-6})$alkoxy, phenyl, pyridinyl, and naphthyl groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono- or independently plurisubstituted with $(C_{1-8})$alkyl; and p is 0 to 3;

$R^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsulfonyl; phenylsulfonyl; aryl; heteroaryl; where the aryl and heteroaryl groups are optionally mono- or independently plurisubstituted with $R^7$;

c) a group of the formula:

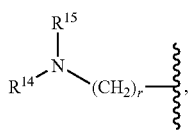

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and r is 2 to 6;

d) a group of the formula:

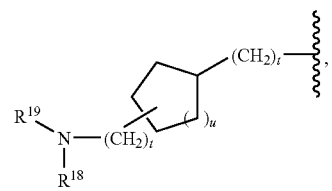

where $R^{18}$ and $R^{19}$ are independently hydrogen; $(C_{1-8})$alkyl; $(C_{1-6})$alkylcarbonyl; di-$(C_{1-6})$alkylaminocarbonyl; benzyl; benzothiazole; benzoyl; pyridine; pyrimidine; phenyl; phenylaminocarbonyl; alkylsulfonyl; or phenylsulfonyl; where the benzyl, benzoyl, benzothiazole, pyridine, pyrimidine, phenyl, phenylaminocarbonyl, alkylsulfonyl, and phenylsulfonyl groups are optionally mono- or independently di-substituted with $R^{12}$; or $R^{18}$ and $R^{19}$ together form a $(C_{3-12})$cycloalkyl ring; each t is independently 0 to 6; and u is 0 to 3;

e) a group of the formula:

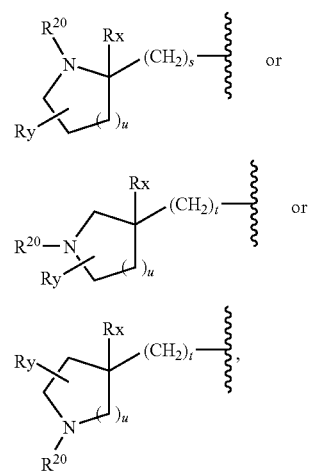

where $R^{20}$ is an N-protecting group or is $(C_{1-8})$alkyl; $(C_{1-6})$alkylcarbonyl; di-$(C_{1-6})$alkylaminocarbonyl; $(C_{3-8})$cycloalkylcarbonyl; benzyl; benzoyl; $(C_{1-6})$alkyloxycarbonyl; aralkyloxycarbonyl, pyridine; pyrimidine; phenyl; phenyl substituted thiazole ring; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; $R_x$ is hydrogen; alkyl; cycloalkyl; alkenyl; cycloalkylalkyl; aryl; aralkyl; heterocyclyl; or heterocyclylalkyl, each optionally mono- or independently di-substituted with $R^{12}$; $R_y$ is absent or is halogen, $(C_{1-8})$alkyl, $(C_{1-8})$alkoxy, O-alkylcarboxylate, O-aralkylcarboxylate, N-alkylcarboxamido, N-aralkylcarboxamido; or phenyl;

s is 1 to 6; t is 0 to 6; and u is 0 to 3.

In some embodiments of the present methods, $R^1$ is a group of the formula:

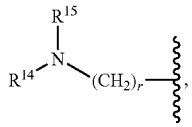

where $R^{14}$ and $R^{15}$ are independently an N-protecting group; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylamino-carbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring or N-protecting group; or one of $R^{14}$ and $R^{15}$ is hydrogen; and r is 2 to 6. In some such embodiments, r is 2, 3 or 4. In other such embodiments, $R^{14}$ and $R^{15}$ are independently methyl, ethyl, benzyl, Cbz, Boc, Fmoc, Alloc, Teoc, acetyl, pivaloyl, benzoyl, cyclohexylcarbonyl, phenylsulfonyl, or one of $R^{14}$ and $R^{15}$ is hydrogen and the other is Cbz, Boc, Fmoc, Alloc, Teoc, acetyl, pivaloyl, benzoyl, cyclohexylcarbonyl, phenylsulfonyl.

In other embodiments, $R^1$ is a group of the formula:

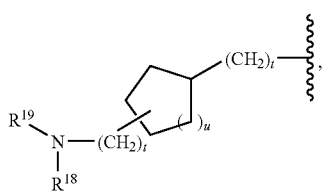

where $R^{18}$ and $R^{19}$ are independently an N-protecting group, $(C_{1-8})$alkyl; $(C_{1-6})$alkylcarbonyl; di-$(C_{1-6})$alkylaminocarbonyl; benzyl; benzothiazole; benzoyl; pyridine; pyrimidine; phenyl; phenylaminocarbonyl; alkylsulfonyl; or phenylsulfonyl; where the benzyl, benzoyl, benzothiazole, pyridine, pyrimidine, phenyl, phenylaminocarbonyl, alkylsulfonyl, and phenylsulfonyl groups are optionally mono- or independently di-substituted with $R^{12}$; or one of $R^{18}$ and $R^{19}$ is hydrogen; or $R^{18}$ and $R^{19}$ together form a $(C_{3-12})$cycloalkyl ring or N-protecting group; each t is independently 0 to 6; and u is 0 to 3. In some such embodiments, t at each occurrence is independently 0, 1, or 2. In other such embodiments, $R^{18}$ and $R^{19}$ are independently methyl, ethyl, benzyl, Cbz, Boc, Fmoc, Alloc, Teoc, acetyl, pivaloyl, benzoyl, cyclohexylcarbonyl, phenylsulfonyl, or one of $R^{18}$ and $R^{19}$ is hydrogen and the other is Cbz, Boc, Fmoc, Alloc, Teoc, acetyl, pivaloyl, benzoyl, cyclohexylcarbonyl, phenylsulfonyl.

In still other embodiments, $R^1$ is a group of the formula:

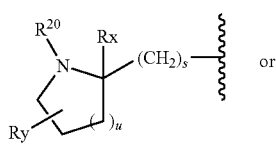

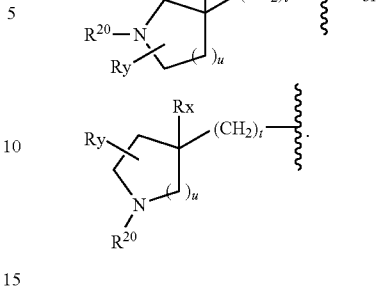

where $R^{20}$ is an N-protecting group or is $(C_{1-8})$alkyl; $(C_{1-6})$alkylcarbonyl; di-$(C_{1-6})$alkylaminocarbonyl; $(C_{3-8})$cycloalkylcarbonyl; benzyl; benzoyl; $(C_{1-6})$alkyloxycarbonyl; aralkyloxycarbonyl, pyridine; pyrimidine; phenyl; phenyl substituted thiazole ring; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently pluri-substituted with $R^{12}$; $R_x$ is hydrogen; alkyl; cycloalkyl; alkenyl, cycloalkylalkyl, aryl, aralkyl, heterocyclyl, or heterocyclylalkyl, each optionally mono- or independently plurisubstituted with $R^{12}$; $R_y$ is absent or is halogen, $(C_{1-8})$alkyl, $(C_{1-8})$alkoxy, O-alkylcarboxylate, O-aralkylcarboxylate, N-alkylcarboxamido, N-aralkylcarboxamido; or phenyl; s is 1 to 6; t is 0 to 6; and u is 0 to 3. In some such embodiments, $R^{20}$ is benzyl, Cbz, Boc, Fmoc, Alloc, Teoc, acetyl, pivaloyl, benzoyl, cyclohexylcarbonyl, or phenylsulfonyl. In some such embodiments, u is 1 or 2, and/or t is 0 or 1, and/or $R_y$ is absent. In still other such embodiments, $R_x$ is hydrogen, methyl, trifluoromethyl, ethyl, pentafluoroethyl, propyl, butyl, phenyl or benzyl, wherein the phenyl and benzyl are optionally perfluorinated or substituted with 1, 2 or 3 groups independently selected from F, Cl, Br, I, R', OR', CN, SH, $NO_2$, $NR'_2$, COOR', $CF_3$, $OCF_3$, SR', S(O)R', or $S(O)_2R'$, wherein R' is H or $C_{1-4}$ alkyl optionally substituted with one or more groups consisting of F and Cl. In certain embodiments, $R_y$ is absent. In some embodiments, $R^1$ is hydrogen or a substituted or unsubstituted alkyl, aralkyl, or heterocyclylalkyl. When $R^1$ is substituted with one or more functional groups, the functional groups may be protected by additional protecting groups that are the same or different from $Pr^1$ and which may be removed simultaneously with $Pr^1$ or separately or sequentially from $Pr^1$. An especially preferred $R^1$ group having the foregoing pyrrolidinyl configuration, and having a protecting group $Pr^1$ bound to the pyrrolidinyl nitrogen is:

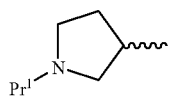

wherein the squiggle line indicates an R or S configuration or mixture thereof.

In still other embodiments of the present methods, $R^1$ is alkyl; alkenyl; alkynyl; cycloalkyl; cycloalkylalkyl; bicycloalkyl; tricycloalkyl; alkylcycloalkyl; hydroxyalkyl; hydroxyalkylcycloalkyl; hydroxycycloalkyl; hydroxybicycloalkyl; hydroxytricycloalkyl; bicycloalkylalkyl; alkylbicycloalkyl; alkylthioalkyl; arylalkylthioalkyl; cycloalkenyl; aryl, aralkyl; heteroaryl; heteroarylalkyl; cycloheteroalkyl or cycloheteroalkylalkyl; all optionally mono- or independently plurisubstituted with halogen, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonyl-amino, alkoxycarbonylamino, alkylsulfonyl, aminosulfinyl, aminosulfonyl, alkylsulfinyl, sulfonamido or sulfonyl. For example, $R^1$ can be methyl, ethyl, n-propyl, i-propyl, n-butyl, i-butyl, s-butyl, t-butyl, n-pentyl, i-pentyl, s-pentyl, cyclopropyl, cyclobutyl, cyclopentyl, cyclopentylmethyl, cyclohexyl, cyclohexylmethyl, cyclohexylethyl, or 1-cyclohexyleth-1-yl, each optionally mono- or independently pluri-substituted with halogen or hydroxy.

The coupling is typically conducted in the presence of solvent. Suitable solvents include water, tetrahydrofuran, 2-methyltetrahydrofuran, dichloromethane, dimethylformamide, or a mixture of any two or more thereof. The exact choice of solvent will be dictated by the choice of coupling reagent or Formula I intermediate (e.g. acid chloride, azide, active ester, mixed anhydride) used in the method. The starting materials and reagents should all be soluble in the solvent. It is convenient but not necessary to choose a solvent or solvent system that will enable easy separation of the desired product from spent reagents. Precipitation of spent reagent is a convenient method for performing such separation. Selection of an appropriate solvent is well within the skill of the ordinary artisan.

A wide variety of N-protecting groups may be employed in methods of the invention. In some embodiments, N-protecting group $Pr^1$ can be benzyl, Cbz, Boc, Fmoc, Alloc, or Teoc. In some embodiments, $Pr^1$ is Cbz and is removed by hydrogenolysis (e.g., $H_2$ with Pd/C, $Pd(OH)_2$, or Pd black). In other embodiments, $Pr^1$ is Boc and is removed by acidolysis (e.g., 4 N HCl/dioxane, 30% TFA/dichloromethane, or 95% TFA/water). In addition, N-protecting groups may be used to protect certain amine-containing $R^1$ groups. In such instances, $Pr^1$ and the additional N-protecting group(s) of $R^1$ may be the same or different. The methods disclosed herein therefore further include removing $Pr^1$ together with or separately from any N-protecting group(s) of $R^1$.

As indicated above, $R^2$ and $R^3$ are independently or together a group that can be hydrolyzed to hydroxyl. For example, $R^2$ and $R^3$ may be independently methoxy, ethoxy, n-propoxy, i-propoxy, or n-butoxy; or together may be 1,2-dioxaethylene, 1,3-dioxapropylene, 2,3-dimethyl-2,3-dioxabutane, or pinanedioxy. Methods of the invention further include hydrolyzing $R^2$ and $R^3$ to hydroxyls. The hydrolysis may be carried out, for example, in the presence of phenyl boronic acid, water, and an organic solvent that is tertbutylmethylether, 2-methyltetrahydrofuran, or a mixture thereof.

The reaction conditions will depend upon the reagents and method for obtaining the amide bond formation. Typically the coupling reaction will be conducted at or about ambient temperature and under atmospheric pressure. If significant heat is generated by the coupling reaction, the reaction may be cooled by means such as a water bath or ice bath.

The course of the coupling reaction may be followed by wet chemistry or spectrographic analysis. Wet chemistry techniques include titration of aliquots of the reaction mixture to determine the presence or absence of acid or base that would be indicative of the amine and/or acid starting materials. Similarly, the presence or absence of spent coupling reagent such as spent DCC can be determined by simple observation if the solvent system is appropriately chosen so that spent DCC precipitates.

Following the completion of the coupling reaction, the protected pyrrolidine product may be isolated and purified by routine techniques. These include neutralization of acidic side products or byproducts that may be present in the reaction mixture, filtration of the reaction mixture to remove insoluble spent reagent, extraction using two phase extraction techniques such as methylene chloride and water, methanol or a mixture thereof. Further purification can be accomplished by column chromatography, high pressure liquid chromatography, precipitation optionally in combination with salt formation, formation of chiral salts for further optical resolution of optical isomers and the use of other chemical techniques for purification of organic compounds containing amide and amine groups. Discussion of such purification techniques as well as details for the corresponding organic reactions may be found in "Advanced Organic Chemistry", $4^{th}$ Ed., Jerry March, Wiley Interscience, New York, N.Y., 1992 as well as in "Organic Synthesis", Collective Volumes 1-11, Gilman et al., Editors, Wiley Interscience, New York, N.Y., 1998.

DEFINITIONS

The following abbreviations are used herein:

| | |
|---|---|
| BOP: | Benzotriazol-1-yloxytris(dimethylamino)phosphonium hexafluorophosphate |
| BOP-Cl: | Bis(2-oxo-3-oxazolidinyl)phosphinic chloride |
| DCC: | Dicyclohexylcarbodiimide |
| DCM: | Dichloromethane |
| DIC: | Diisopropylcarbodiimide |
| DIEA: | N,N-Diisopropylethylamine |
| DMAP: | N,N-dimethylaminopyridine |
| DMF: | N,N-Dimethylformamide |
| DMSO: | Dimethylsulfoxide |
| EDCI: | 1-ethyl-3-(3'-dimethylaminopropyl)carbodiimide hydrochloride |
| EtOAc: | Ethyl acetate |
| $Et_3N$, TEA: | Triethylamine |
| HATU: | 2-(7-Aza-1H-benzotriazole-1-yl)-1,1,3,3-tetramethyluronium hexafluorophosphate |
| HOAt: | 1-Hydroxy-7-azabenzotriazole |
| HOBt: | 1-Hydroxybenzotriazole |
| MeOH: | Methanol |
| mL: | Milliliter(s) |
| mmol: | Millimole(s) |
| MS: | Mass spectroscopy |
| μL: | microliter(s) |
| NMM: | N-methylmorpholine |
| NMR: | Nuclear magnetic resonance |
| PyBOP: | Benzotriazole-1-yl-oxy-tripyrrolidinophosphonium hexafluorophosphate |
| PyBrOP: | Bromo-tris-pyrrolidinophosphonium hexafluorophosphate |
| TFA: | Trifluoroacetic acid |

The following terms are used herein as defined below.

The term "DPP-IV" denotes dipeptidyl peptidase IV (EC 3.4.14.5; DPP-IV), also known as "CD-26." DPP-IV preferentially cleaves a dipeptide from the N terminus of a polypeptide chain containing a proline or alanine residue in the penultimate position.

The term "group that can be hydrolyzed to a hydroxy" as used herein refers to groups that can be converted to a hydroxyl group in an aqueous solution. In some embodiments, these groups may be hydrolyzed to a hydroxyl at physiological pH. In certain embodiments, these groups are employed to mask or otherwise protect the boronic acid functionality of compounds of the invention while reactions involving other functional sites of the compound are carried out. Typically, the boronic acid OH groups are protected as boronic acid esters derived from alcohols such as (+)- or (−)-pinanediol; pinacol; 1,2-dicyclohexyl-ethanediol; 1,2-ethanediol; 2,2-diethanolamine; 1,3-propanediol; 2,3-butanediol, diisopropyl tartrate; 1,4-butanediol; diisopropylethanediol; (S,S,)-5,6-decanediol; 1,1,2-triphenyl-1,2-ethanediol; (2R,3R)-1,4-dimethyoxy-1,1,4,4-tetraphenyl-2,3-butanediol; methanol; ethanol; isopropanol; catechol; 1-butanol; and the like. As will be understood by those skilled in the art, alcohols having only a single hydroxy group, such as methanol, form diesters having the structure —B(OR)$_2$ in which R is the organic moiety from the alcohol (e.g., —B(OCH$_3$)$_2$). By comparison, diols such as pinacol form cyclic boronic diesters with —B(OH)$_2$ in which the organic moiety (e.g., —C(CH$_3$)$_2$—C(CH$_3$)$_2$—) is attached to both oxygens.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in T. W. Greene, P. G. Wuts, "Protective Groups In Organic Synthesis, 3$^{rd}$ Ed." (John Wiley & Sons, New York (1999)), which is hereby incorporated by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α-α-di methyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, 9-fluorenylmethyloxycarbonyl (Fmoc), t-butyloxycarbonyl (Boc) and benzyloxycarbonyl (Cbz).

In general, "substituted" refers to an organic group as defined below in which one or more bonds to a hydrogen atom contained therein are replaced by a bond to non-hydrogen or non-carbon atoms such as, but not limited to, a halogen (i.e., F, Cl, Br, and I); an oxygen atom in groups such as hydroxyl groups, alkoxy groups, aryloxy groups, aralkyloxy groups; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, N-oxides, hydrazides, azides, and enamines; and other heteroatoms in various other groups. Substituted alkyl, alkenyl, alkynyl, cycloalkyl, and cycloalkenyl groups as well as other substituted groups also include groups in which one or more bonds to a carbon(s) or hydrogen(s) atom are replaced by one or more bonds, including double or triple bonds, to a heteroatom such as, but not limited to, oxygen in carbonyl (oxo), carboxyl, ester, amide, imide, urethane, and urea groups; and nitrogen in imines, hydroxyamines, oximes, hydrazones, amidines, guanidines, and nitriles.

Substituted ring groups such as substituted aryl, heterocyclyl and heteroaryl groups also include rings and fused ring systems in which a bond to a hydrogen atom is replaced with a bond to a carbon atom. Therefore, substituted aryl, heterocyclyl and heteroaryl groups may also be substituted with alkyl, alkenyl, and alkynyl groups as defined below.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, t-butyl, neopentyl, isopentyl, and 2,2-dimethylpropyl groups. Representative substituted alkyl groups may be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-, 2,5- or 2,6-disubstituted cyclohexyl groups or mono-, di- or tri-substituted norbornyl or cycloheptyl groups, which may be substituted with, for example, amino, hydroxy, cyano, carboxy, nitro, thio, alkoxy, and halogen groups.

Cycloalkylalkyl groups are alkyl groups as defined above in which a hydrogen or carbon bond of the alkyl group is replaced with a bond to a cycloalkyl group as defined above.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halogen groups, bonded to one of the ring members. Rather, groups such as tolyl are referred to as substituted aryl groups. Representative substituted aryl groups may be mono-substituted or substituted more than once, such as, but not limited to, 2-, 3-, 4-, 5-, or 6-substituted phenyl or naphthyl groups, which may be substituted with groups such as those listed above.

Aralkyl groups are alkyl groups as defined above in which a hydrogen or carbon bond of an alkyl group is replaced with a bond to an aryl group as defined above. Representative aralkyl groups include benzyl groups and fused (cycloalkylaryl)alkyl groups such as 4-ethyl-indanyl.

Heterocyclyl groups include aromatic and non-aromatic ring compounds containing 3 or more ring members, of which, one or more is a heteroatom such as, but not limited to, N, O, and S. In some embodiments, heterocyclyl groups include 3 to 20 ring members, whereas other such groups have 3 to 15 ring members. The phrase "heterocyclyl group" includes fused ring species including those comprising fused aromatic and non-aromatic groups. The phrase also includes polycyclic ring systems containing a heteroatom such as, but not limited to, quinuclidyl. However, the phrase does not include heterocyclyl groups that have other groups, such as alkyl or halogen groups, bonded to one of the ring members. Rather, these are referred to as "substituted heterocyclyl groups". Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthenyl, adeninyl, guanidyl, quinolinyl, isoquinolinyl, tetrahydroquinolinyl, quinoxalinyl, and quinazolinyl groups. Representative substituted heterocyclyl groups may be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthenyl, adeninyl, guanidyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups". Representative substituted heteroaryl groups may be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f] azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f] azepine-4-yl, 10,1,1-dihydro-5H-dibenz[b,f]azepine-5-yl), and the like.

Heterocyclylalkyl groups are alkyl groups as defined above in which a hydrogen or carbon bond of an alkyl group is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroaralkyl groups are alkyl groups as defined above in which a hydrogen or carbon bond of an alkyl group is replaced with a bond to a heteroaryl group as defined above.

The term "alkoxy" refers to an oxygen atom connected to an alkyl group as defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

The terms "aryloxy" and "arylalkoxy" refer to, respectively, an aryl group bonded to an oxygen atom and an aralkyl group bonded to the oxygen atom at the alkyl. Examples include but are not limited to phenoxy, naphthyloxy, and benzyloxy.

The term "alkanoyl", alone or as part of another group, refers to alkyl linked to a carbonyl group.

The term "amine" (or "amino") includes primary, secondary, and tertiary amines having, e.g., the formula —NR$^6$R$^7$. R$^6$ and R$^7$ at each occurrence are independently hydrogen, or a substituted or unsubstituted alkyl, alkenyl, alkynyl, cycloalkyl, cycloalkenyl, aryl, aralkyl, heterocyclyl or heterocyclylalkyl group as defined herein. Amines thus include but are not limited to —NH$_2$, alkylamines, dialkylamines, arylamines, alkylarylamines, diarylamines, aralkylamines, heterocyclylamines and the like.

The term "amide" (or "amido") includes C- and N-amide groups, i.e., —C(O)NR$^8$R$^9$, and —NR$^8$C(O)R$^9$ groups, respectively. R$^8$ and R$^9$ are independently hydrogen, or a substituted or unsubstituted alkyl, alkenyl, alkynyl, cycloalkyl, cycloalkenyl, aryl, aralkyl, heterocyclyl or heterocyclylalkyl group as defined herein. Amide groups therefore include but are not limited to carbamoyl groups (—C(O)NH$_2$) and formamide groups (—NHC(O)H).

The term "urethane" (or "carbamyl") includes N- and O-urethane groups, i.e., —NR$^{10}$C(O)OR$^{11}$ and —OC(O)NR$^{10}$R$^{11}$ groups, respectively. R$^{10}$ and R$^{11}$ are independently hydrogen, or a substituted or unsubstituted alkyl, cycloalkyl, aryl, aralkyl, or heterocyclyl group as defined herein.

The term "sulfonamide" (or "sulfonamido") includes S- and N-sulfonamide groups, i.e., —SO$_2$NR$^{12}$R$^{13}$ and —NR$^{12}$SO$_2$R$^{13}$ groups, respectively. R$^{12}$ and R$^{13}$ are independently hydrogen, or a substituted or unsubstituted alkyl, cycloalkyl, aryl, aralkyl, or heterocyclyl group as defined herein. Sulfonamide groups therefore include but are not limited to sulfamoyl groups (—SO$_2$NH$_2$).

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present invention, thus generally described, will be understood more readily by reference to the following examples, which are provided by way of illustration and are not intended to be limiting of the present invention.

EXAMPLES

Example 1

Synthesis of 2-(Benzyloxycarbonyl-R$^1$-amino)-acetic acid methyl ester

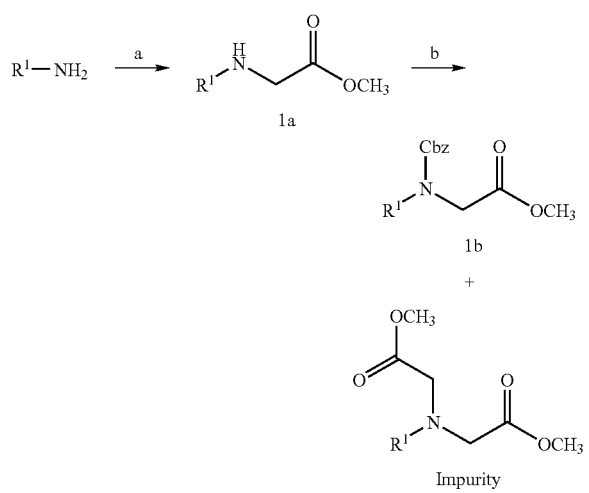

Step a—To a biphasic solution of primary amine (1 equivalent (eq)) dissolved in MTBE and H$_2$O (2:3, to give a 1-1.5 M concentration of amine) containing K$_2$CO$_3$ (4 eq) is added methyl bromoacetate (1.5 eq) with vigorous stirring at room temperature. The reaction is monitored by TLC (5% MeOH in DCM visualized by I$_2$,) and by LCMS. The reaction is typically complete at about t=2 hrs.

Step b—The biphasic solution from step (a) containing 1a is cooled in an ice bath and Cbz-Cl (1 eq) is added. The flask is removed from the ice bath and allowed to stir for an additional 20 min. The reaction is diluted with H$_2$O (3-4 mL/mmol product) and is extracted with MTBE (3×4-5 mL/mmol product). The organic layers were combined and washed with 2 N HCl (3×6-7 mL/mmol product). The solution of 1b was concentrated to ~0.5-1 M and used in the following reaction "as is". This two step procedure enabled the straightforward removal of the impurity shown above. This impurity is difficult to remove using procedures that do not protect the secondary amine after the alkylation reaction. Using the present route the 2 N HCl acidic washes remove the dialkylated impurity.

Example 2

Synthesis of 2-(Benzyloxycarbonyl-R$^1$-amino)-acetic acid

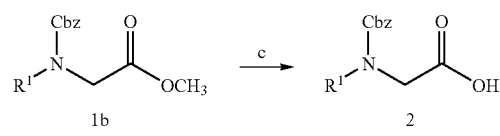

Step c—To a solution of 1b (theoretical 1 eq) in MTBE (~0.5-1 M) is added an aqueous solution containing NaOH (2 eq in H$_2$O, ~2 M). The reaction mixture is heated at reflux for about 2 hrs. The cloudy emulsion is cooled to room temperature and diluted with 0.2N NaOH solution (3-4 mL/mmol product) and additional MTBE (3-4 mL/mmol product). The resulting bi-phasic solution is stirred vigorously for 30 minutes, the organic layer is removed, and the aqueous layer is washed with additional MTBE (3-4 mL/mmol product) and is then acidified with 1N HCl (~2-3 mL/mmol product). The resulting milky white suspension is extracted with MTBE (3×6-7 mL/mmol product) and the organic layers are combined, are washed with brine (40 mL), are dried over Na$_2$SO$_4$, and are concentrated to afford 2, e.g., as a foamy white solid in good yield.

Example 3

Synthesis of (2R)-1-{2-[benzyloxycarbonyl-R$^1$-amino]-acetyl}-pyrrolidine-2-boronic acid (1S,2S,3R,5S)-pinanediol ester

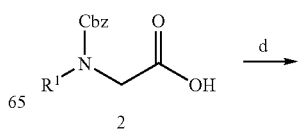

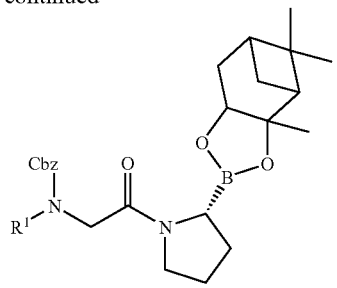

3

Step d—To an ice cooled solution of 2 (1 eq) dissolved in MeTHF (~1 M) and isobutylchloroformate (0.98 eq) is added NMM (1.5 eq) drop-wise over a 2 minute period; a white precipitate typically is formed. This mixture is allowed to stir at 0° C. for 10 minutes followed by addition of solid HCl boroPro-(+)-pinanediol 6B (0.98 eq) along with additional NMM (1.5 eq). The ice bath is removed and the reaction is stirred for 45 minutes before being quenched with NaHCO$_3$ solution (~3-4 mL/mmol product) and extracted with MTBE (3×~15 mL/mmol product). The organic fractions are combined and are washed with 1N HCl (2×~15 mL/mmol product) followed by brine (~15 mL/mmol product), are dried over Na$_2$SO$_4$, and are concentrated to afford 3, as, e.g., a foamy white solid in good yield.

Example 4

Synthesis of (2R)-1-{2-[R$^1$-amino]-acetyl}-pyrrolidine-2-boronic acid (1S,2S,3R,5S)-pinanediol ester

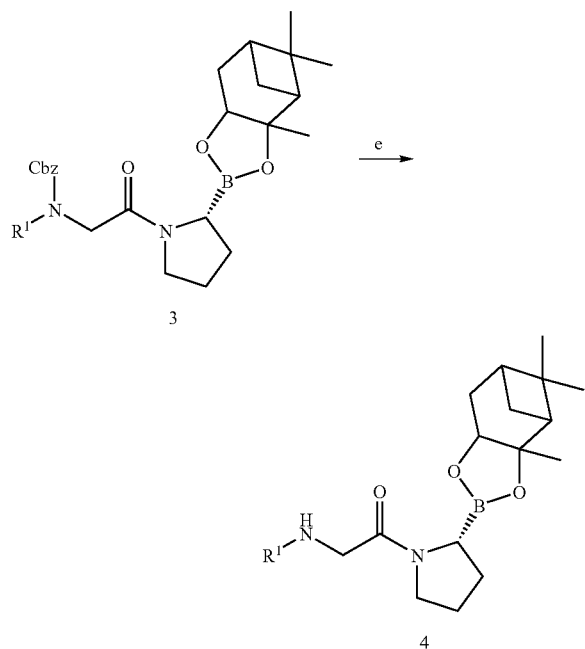

Step e—To a methanolic solution of 3 (1 eq) flushed with copious amounts of N$_2$ (g) is added a catalytic amount of palladium on carbon (10%). The reaction flask is then evacuated under vacuum and H$_2$(g) is introduced by balloon. The flask is once again evacuated under vacuum and H$_2$(g) is again introduced by balloon. This procedure is repeated one more time to ensure complete displacement of any residual gasses with H$_2$. The reaction mixture is stirred vigorously for 2 hours. After TLC (5% MeOH in DCM, made visible by I$_2$) indicates all starting material is consumed, the flask is flushed with N$_2$ (g), is filtered and is concentrated to afford 4 as, e.g., a white solid in near quantitative yield.

Example 5

Synthesis of (2R)-1-{2-[R$^1$-amino]-acetyl}-pyrrolidine-2-boronic acid

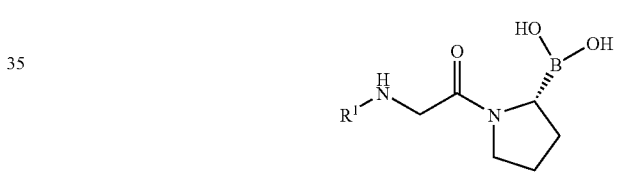

Step f—To a solution of 4 (1 eq) dissolved in water (~0.3-0.5 M) is added phenylboronic acid (1.05 eq) and MTBE (~7-8 mL/mmol reactant). The bi-phasic solution is stirred vigorously. The MTBE layer is periodically removed by decanting and additional MTBE is added followed by vigorous stirring. The deprotection is monitored by LCMS. Additional phenyl boronic acid may be added as needed to force the reaction to completion. The deprotection can be monitored by LCMS. After a number of washing and decanting cycles the deprotection will be complete, and the water layer is then diluted with isopropyl alcohol (~7-8 mL/mmol product) and is concentrated in vacuo. The residue is azeotropically dried 2 more times to remove residual water after which the glassy clear solid is diluted a final time in isopropyl alcohol (1 mL/mmol product) and to this is added isopropyl acetate (~7-8 mL/mmol product). Upon addition of the isopropyl acetate, a white solid typically appears on the sides of the flask. The solvents are then removed in vacuo to give a white precipitate. The precipitate is scraped from the sides of the flask and is suspended in isopropyl acetate (~4-5 mL/mmol product) and is concentrated in vacuo. This process is repeated 2 additional times, and is followed by drying under high vacuum to give 5 as, e.g., a white solid.

Example 6

Alternative Synthetic Procedure for Synthesis of (2R)-1-{2-[R¹-amino]-acetyl}-pyrrolidine-2-boronic acid

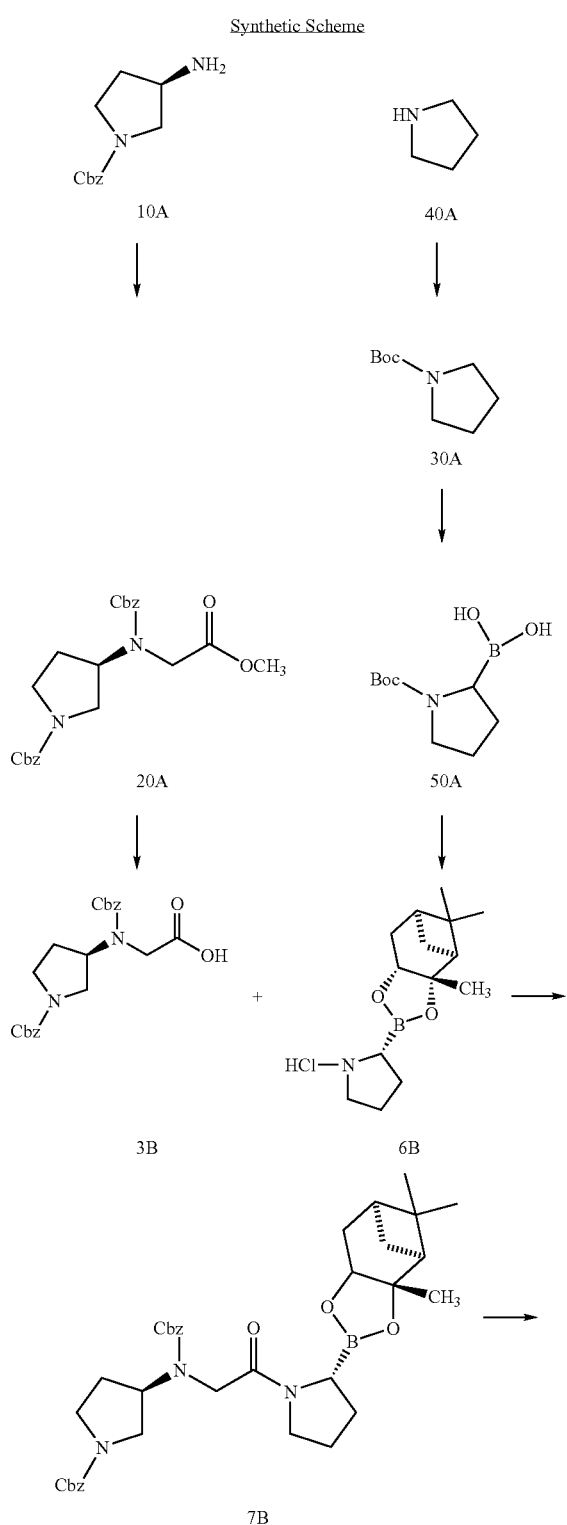

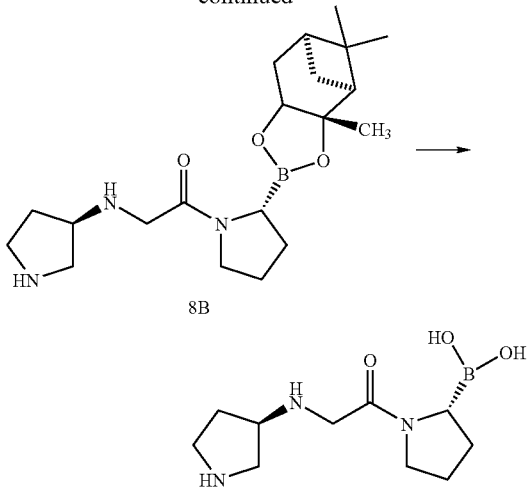

tartaric acid salt
9T

Example 6A 3-(R)-(benzyloxycarbonyl-carboxymethyl-amino)-pyrrolidine-1-carboxylic acid benzyl ester 3B Into reactor A was charged (R)—Cbz-3-aminopyrrolidine hydrochloride 10A (1 kg), MTBE (3 kg), and a solution of potassium carbonate (2.6 kg) in water (5 kg). The mixture was cooled to between 0-10° C. then methyl bromoacetate (0.9 kg) added with stirring followed by MTBE (0.2 kg) then the reactor temperature was warmed to between 20-25° C. After 4 hours the reactor was cooled to between 0-10° C., benzyl chloroformate added while maintaining the batch temperature below 15° C. followed by MTBE (0.2 kg). The mixture was warmed to between 20-25° C. and stirred for 1 hour. Stirring was stopped, the organic layer was isolated, and washed with water (2 kg), then 3 N hydrochloric acid (2 L) two times to yield intermediate 20A. The reactor was charged with 50% w/w sodium hydroxide (1 kg) and water (4 kg), heated to reflux (~55° C.) for 2 hours then cooled to between 20-25° C. The organic phase was discarded, and the aqueous phase washed twice with MTBE (2 kg), cooled to between 0-5° C. then treated with 37% w/w hydrochloric acid (1.2 kg) while maintaining a batch temperature below 35° C. The aqueous phase was extracted two times with dichloromethane (2.7 kg). The organic phase was collected and concentrated to a volume of approximately 1 litre, then diluted with dichloromethane (4 kg) and concentrated to a volume of approximately 1 litre two times to yield a solution of 3-(R)-(benzyloxycarbonyl-carboxymethyl-amino)-pyrrolidine-1-carboxylic acid benzyl ester 3B in dichloromethane.

Example 6b (2R)-1-{2-[(3R)-pyrrolidinylamino]-acetyl}-pyrrolidine-2-boronic acid (1S,2S,3R,5S)-pinanediol ester 8B (2R)-boroPro-(1S,2S,3R,5S)-pinanediol ester HCl salt 6B (16.56 kg), 1-hydroxybenzotriazole (9.36 kg), methylmorpholine (20.64 kg), 3-(R)-(benzyloxycarbonyl-carboxymethyl-amino)-pyrrolidine-1-carboxylic acid benzyl ester 3B (98.36 kg) and dichloromethane (213.6 kg) were charged to the reactor under a nitrogen atmosphere, cooled to 0-5° C. then EDCI (12.24 kg) added and the mixture was stirred while maintaining the temperature at 0-5° C. After 4 hours the reactor was warmed to 20-25° C. and stirring continued for 6 hours. The reaction mixture was distilled under vacuum while maintaining the reactor temperature no higher than 25° C. to a final volume of 110 litre. The reactor was charged with water (96 kg) and citric acid (1.2 kg), stirred for 15 minutes then the aqueous layer discarded. The reactor was charged with water (225.6 kg) and sodium bicarbonate (15.36 kg), stirred for 15 minutes then the aqueous layer discarded. The reactor was charged with ethyl acetate (283.2 kg), the temperature was stabilized at 20-25° C., then an aqueous 7% sodium bicarbonate solution (134.4 kg) added and the mixture stirred for 10 minutes then the aqueous layer discarded. This process was repeated with aqueous 7% sodium bicarbonate solution (64.8 kg). The reactor was charged with water (96 kg) and citric acid (1.2 kg), stirred for 10 minutes then the aqueous layer discarded. The reaction mixture was concentrated under vacuum at 20-35° C. to a final volume of approximately 41 litres.

The reactor, containing 7B was charged with methanol (48 kg), the temperature stabilized at 20-25° C., a nitrogen atmosphere established. In a separate reactor under a nitrogen atmosphere 5% palladium on carbon (1.92 kg) and methanol (100.8 kg) was charged then the methanol reaction mixture was added. The reactor was purged with hydrogen, a positive pressure of hydrogen maintained with stirring. After 4 hours a nitrogen atmosphere was established and the reactor charged with anhydrous sodium sulfate (40.8 kg). The reaction mixture was filtered and the filtrate and reactor rinsed with methanol (24 kg). The reaction mixture was concentrated under vacuum maintaining the temperature between 20-35° C. to a final volume of approximately 48 litres. A solvent switch performed with two cycles consisting of adding ethyl acetate (211 kg) then concentrating under vacuum while maintaining the reactor temperature at 20-35° C. to a final volume of approximately 79 litres. The reaction mixture was cooled to between −5 to −10° C. then filtered. The cake was dried under vacuum at a maximum temperature of 40° C. to yield the coupled material (2R)-1-{2-[(3R)-pyrrolidinylamino]-acetyl}-pyrrolidine-2-boronic acid (1S,2S,3R,5S)-pinanediol ester 8B (14.98 kg).

Example 6c

Mono-L-tartrate salt of (2R)-1-{2-[(3R)-pyrrolidin-3-ylamino]-acetyl}-pyrrolidine-2-boronic acid 9T (2R)-1-{2-[(3R)—Pyrrolidin-3-ylamino]-acetyl}-pyrrolidine-2-boronic acid (1S,2S,3R,5S)-pinanediol ester 8B (12.5 kg), L-tartaric acid (5 kg) and purified water (25 kg) were charged to a reactor under a nitrogen atmosphere. The reaction mixture was stirred for 1 hour at less than 30° C. for 1 hour, then phenylboronic acid (4.13 kg) and MTBE (46.3 kg) added and the mixture stirred at 15-25° C. for 2 hours. The aqueous phase was collected, treated with 2-methyltetrahydrofuran (53.8 kg) stirred for 10 minutes then the aqueous phase isolated, this was repeated 4 times. The aqueous phase was concentrated under vacuum with a temperature of between 35-50° C. for not less than 2 hours. The concentrated aqueous phase was freeze dried to yield the mono-L-tartrate salt of (2R)-1-{2-[(3R)-pyrrolidin-3-ylamino]-acetyl}-pyrrolidine-2-boronic acid 9T.

While the invention has been described and exemplified in sufficient detail for those skilled in this art to make and use it, various alternatives, modifications, and improvements will be apparent to those skilled in the art without departing from the spirit and scope of the claims.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

All references and citations made herein are incorporated herein as if fully reproduced. Any and all passages from such references and citations are considered applicable for any aspect, feature or detail described herein.

Other embodiments are set forth within the following claims.

What is claimed is:

1. A method comprising
coupling a compound of Formula I

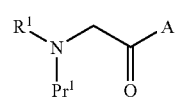

I with a compound of Formula II

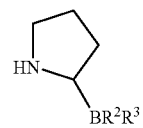

II to provide a compound of Formula III

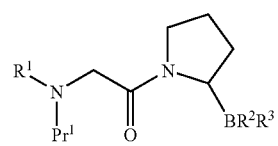

III wherein,

A is OH or a group which may be displaced by an amine;

$Pr^1$ is an N-protecting group;

$R^1$ is a substituted or unsubstituted cycloalkyl, cycloalkylalkyl, cycloalkenyl, cycloalkenylalkyl, aryl, heterocyclyl, heterocyclylalkyl, heteroaryl, or heteroarylalkyl group; and $R^2$ and $R^3$ are independently or together a group that can be hydrolyzed to hydroxyl.

2. The method of claim 1 further comprising preparing the compound of Formula I by alkylating a compound of Formula IV, $R^1$—$NH_2$, in the presence of base with a compound of Formula V, L-$CH_2$—COOR', wherein L is a leaving group; $R^1$ is as previously defined, and R' is a carboxyl-protecting group; to provide a compound of Formula VI, $R^1$—NH—$CH_2$—COOR', protecting the secondary amine to provide a compound of Formula VII, $R^1$—N($Pr^1$)—$CH_2$—COOR', and converting a compound of Formula VII to a compound of Formula I.

3. The method of claim 2 wherein L is Cl, Br, I, mesylate, or triflate.

4. The method of claim 2 wherein R' is a substituted or unsubstituted alkyl, alkenyl, or aralkyl group.

5. The method of claim 4 wherein R' is methyl, ethyl, t-butyl, allyl, or benzyl.

6. The method of claim 2 wherein the base is sodium carbonate, potassium carbonate, or cesium carbonate.

7. The method of claim 6 wherein the compound of Formula VII is hydrolyzed with base to the compound of Formula I wherein A is OH.

8. The method of claim 2 wherein the protection of the secondary amine is carried out with a substituted or unsubstituted alkoxychloroformate or aryloxychloroformate.

9. The method of claim 1 or 2 wherein A is OH and the coupling is conducted using a coupling reagent.

10. The method of claim 9 wherein the coupling reagent is DCC, DIC, EDCI, HATU, BOP, BOP-Cl, PyBOP, or PyBrOP.

11. The method of claim 9, wherein the coupling is conducted in the presence of a coupling additive.

12. The method of claim 11 wherein the coupling additive is HOBt, HOAt, or DMAP.

13. The method of claim 1 wherein the coupling is conducted in the presence of a base.

14. The method of claim 13 wherein the base is triethylamine, diisopropylethylamine, or N-methylmorpholine.

15. The method of claim 1 or 2 wherein A is selected from imidazolyl, F, Cl, Br, I, azide, pentafluorophenoxy, p-nitrophenoxy, N-oxysuccinimide, or OC(O)OR, wherein R is substituted or unsubstituted $C_{1-8}$ alkyl.

16. The method of claim 1 or 2 wherein $Pr^1$ is benzyl, Cbz, Boc, Fmoc, Alloc, or Teoc.

17. The method according to claim 1 wherein $R^1$ is cycloalkyl, cycloalkylalkyl, cycloalkenyl, cycloalkenylalkyl, aryl, heterocyclyl, heterocyclylalkyl, heteroaryl, or heteroarylalkyl group.

18. The method of any one of claims 1 and 2 wherein $R^1$ is a) $(C_{3-12})$ cycloalkyl; or $(C_{3-12})$cycloalkenyl; where the cycloalkyl and cycloalkenyl groups are optionally mono- or independently plurisubstituted with $R^6$;

$R^6$ is $(C_{1-6})$alkyl; $(C_{1-6})$alkoxy; cycloalkyl; carboxy; acetamido; cyano; nitro; halogen; hydroxy; hydroxy$(C_{1-6})$ alkyl; hydroxymethyl; trifluoromethyl; trifluoromethoxy; sulfamoyl; sulfonamido; carbamoyl; aryl; heteroaryl, where the aryl and heteroaryl groups are optionally mono- or independently plurisubstituted with $R^7$; amino, where the amino group is optionally mono- or independently plurisubstituted with $R^8$; —$SOR^8$; —$SO_2R^8$; —$COR^8$; —$CO_2R^8$, —$CONHR^8$; —CON$(R^8)_2$; —$OR^8$; or —S—$R^8$;

$R^7$ is halogen; $(C_{1-10})$alkyl, $(C_{1-10})$alkoxy, $(C_{1-10})$alkylamino, $(C_{1-10})$ dialkylamino, benzyl, benzyloxy, hydroxyl$(C_{1-6})$alkyl; hydroxymethyl; nitro; trifluoromethyl, trifluoromethoxy, trifluoromethylthio, N-hydroxyimino, cyano, carboxy, acetamido, hydroxyl, sulfamoyl, sulfonamido or carbamoyl;

$R^8$ is $(C_{1-10})$alkyl; $(C_{2-10})$alkenyl; $(C_{2-10})$alkynyl; $(C_{3-10})$ cycloalkyl; $(C_{5-10})$cycloalkenyl; benzyl; phenethyl; aryl; or heteroaryl, where the alkyl, alkenyl, alkynyl, cycloalkyl, cycloalkenyl groups are optionally mono- or independently plurisubstituted with aryl or heteroaryl where the aryl and heteroaryl groups are optionally mono- or independently plurisubstituted with $R^7$; and where the aryl and heteroaryl groups are optionally mono- or independently plurisubstituted with $R^7$;

b) aryl optionally fused to a $(C_{3-10})$cycloalkyl; or heteroaryl optionally fused to a $(C_{3-10})$cycloalkyl, where the aryl and heteroaryl groups are optionally mono- or independently plurisubstituted with $R^7$;

c) indanyl; 1,2,3,4-tetrahydronaphthyl; $(CH_2)_j$adamantyl in which j is 0-3; or a [2.2.1] or [3.1.1] bicyclic carbocyclic moiety, including (4-pentylbicyclo[2.2.2]oct-1-yl) amine, where the indanyl, 1,2,3,4-tetrahydronaphthyl, $(CH_2)_j$ adamantyl, and [2.2.1] or [3.1.1] bicyclic carbocyclic moieties are optionally mono- or independently plurisubstituted with hydroxy, $(C_{1-8})$alkyl, $(C_{1-8})$ alkoxy, $(C_{1-8})$alkanoyloxy, or $R^9R^{10}N$—CO—O—, where $R^9$ and $R^{10}$ are independently $(C_{1-8})$alkyl, or phenyl, where the alkyl and phenyl groups are optionally mono- or independently plurisubstituted with $(C_{1-8})$ alkyl, $(C_{1-8})$alkoxy, halogen, or trifluoromethyl, or $R^9$ and $R^{10}$ together are $(C_{3-6})$alkylene;

d) $R^{11}(CH_2)_p$— where $R^{11}$ is 2-oxopyrrolidinyl; $(C_{1-8})$cycloalkyl; [3.3.3] bicyclic carbocyclic moiety; pyridinyl; cyclohexenyl; or adamantyl, where the 2-oxopyrrolidinyl, pyridinyl, groups are optionally mono- or independently di- or independently trisubstituted with $R^{12}$; and where the [3.3.3] bicyclic carbocyclic moiety is optionally mono- or independently plurisubstituted with $(C_{1-8})$alkyl; and p is 0 to 3;

$R^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsulfonyl; phenylsulfonyl; aryl; heteroaryl, where the aryl and heteroaryl groups are optionally mono- or independently plurisubstituted with $R^7$;

h) a group of the formula:

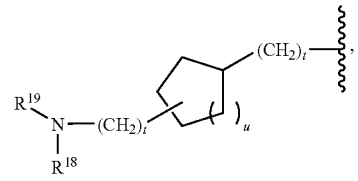

where $R^{18}$ and $R^{19}$ are independently hydrogen; $(C_{1-8})$alkyl; $(C_{1-6})$alkylcarbonyl; di-$(C_{1-6})$alkylaminocarbonyl; benzyl; benzothiazole; benzoyl; pyridine; pyrimidine; phenyl; phenylaminocarbonyl; alkylsulfonyl; or phenylsulfonyl; where the benzyl, benzoyl, benzothiazole, pyridine, pyrimidine, phenyl, phenylaminocarbonyl, alkylsulfonyl, and phenylsulfonyl groups are optionally mono- or independently di-substituted with $R^{12}$; or $R^{18}$ and $R^{19}$ together form a $(C_{3-12})$ cycloalkyl ring; each t is independently 0 to 6; and u is 0 to 3;

i) a group of the formula:

$$(\text{phenyl-}CH_2-C(CH_3)_2-),$$

where the phenyl group is optionally mono- or independently plurisubstituted with $R^{12}$;

j) a group of the formula:

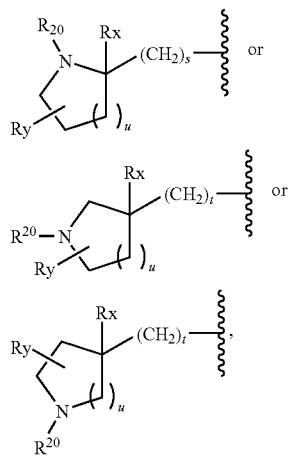

where $R^{20}$ is an N-protecting group or is $(C_{1-8})$alkyl; $(C_{1-6})$ alkylcarbonyl; di-$(C_{1-6})$alkylaminocarbonyl; $(C_{3-8})$cycloalkylcarbonyl; benzyl; benzoyl; $(C_{1-6})$alkyloxycarbonyl; aralkyloxycarbonyl, pyridine; pyrimidine; phenyl; phenyl substituted thiazole ring; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; $R_x$ is hydrogen; alkyl; cycloalkyl; alkenyl, cycloalkylalkyl, aryl, aralkyl, heterocyclyl, or heterocyclylalkyl, each optionally mono- or independently di-substituted with $R^{12}$; $R_y$ is absent or is halogen, $(C_{1-8})$alkyl, $(C_{1-8})$alkoxy, O-alkylcarboxylate, O-aralkylcarboxylate, N-alkylcarboxamido, N-aralkylcarboxamido; or phenyl; s is 1 to 6; t is 0 to 6; and u is 0 to 3; or k) a group of the formula:

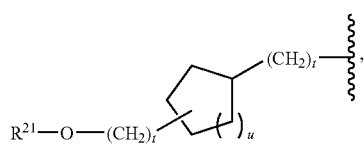

where $R^{21}$ is hydrogen; $(C_{1-8})$alkyl; benzyl; or phenyl; in which the benzyl and phenyl groups are optionally mono- or independently di-substituted on the ring with $R^{12}$; each t is independently 0 to 6; and u is 0 to 3; or l) cycloalkyl; cycloalkylalkyl; bicycloalkyl; tricycloalkyl; alkylcycloalkyl; hydroxyalkylcycloalkyl; hydroxycycloalkyl; hydroxybicycloalkyl; hydroxytricycloalkyl; bicycloalkylalkyl; alkylbicycloalkyl; cycloalkenyl; aryl, aralkyl; heteroaryl; heteroarylalkyl; cycloheteroalkyl or cycloheteroalkylalkyl; all optionally mono- or independently plurisubstituted with halogen, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylamino-carbonyl, alkylaminocarbonyl, alkenylaminocarbonyl, alkylcarbonyloxy, alkylcarbonylamino, arylcarbonylamino, alkylsulfonylamino, alkylaminocarbonyl-amino, alkoxycarbonylamino, alkylsulfonyl, aminosulfinyl, aminosulfonyl, alkylsulfinyl, sulfonamido or sulfonyl.

19. The method of claim 1 wherein $R^1$ is a) aryl optionally fused to a $(C_{3-10})$cycloalkyl; or heteroaryl optionally fused to a $(C_{3-10})$cycloalkyl; where the aryl and heteroaryl groups are optionally mono- or independently plurisubstituted with $R^7$;

$R^7$ is halogen; $(C_{1-10})$alkyl; $(C_{1-10})$alkoxy; $(C_{1-10})$alkylamino; $(C_{1-10})$ dialkylamino; benzyl; benzyloxy; hydroxyl$(C_{1-6})$alkyl; hydroxymethyl; nitro; trifluoromethyl; trifluoromethoxy; trifluoromethylthio; N-hydroxyimino; cyano; carboxy; acetamido; hydroxy; sulfamoyl; sulfonamido; or carbamoyl;

b) $R^{11}(CH_2)_p$— where $R^{11}$ is 2-oxopyrrolidinyl; $(C_{1-8})$cycloalkyl; [3.3.3] bicyclic carbocyclic moiety; pyridinyl; cyclohexenyl; or adamantyl; where the 2-oxopyrrolidinyl, pyridinyl, groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono- or independently plurisubstituted with $(C_{1-8})$alkyl; and p is 0 to 3;

c) a group of the formula:

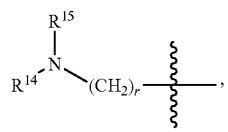

where $R^{14}$ and $R^{15}$ together form a $(C_{3-12})$cycloalkyl ring; and r is 2 to 6;

d) a group of the formula:

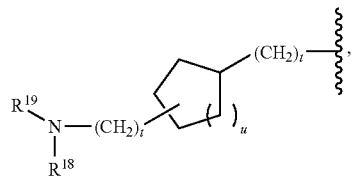

where $R^{18}$ and $R^{19}$ are independently hydrogen; $(C_{1-8})$alkyl; $(C_{1-6})$alkylcarbonyl; di-$(C_{1-6})$alkylaminocarbonyl; benzyl; benzothiazole; benzoyl; pyridine; pyrimidine; phenyl; phenylaminocarbonyl; alkylsulfonyl; or phenylsulfonyl; where the benzyl, benzoyl, benzothiazole, pyridine, pyrimidine, phenyl, phenylaminocarbonyl, alkylsulfonyl, and phenylsulfonyl groups are optionally mono- or independently di-substituted with $R^{12}$; or $R^{18}$ and $R^{19}$ together form a $(C_{3-12})$ cycloalkyl ring; each t is independently 0 to 6; and u is 0 to 3; or e) a group of the formula:

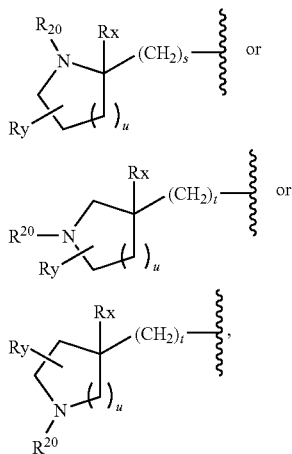

where $R^{20}$ is an N-protecting group or is $(C_{1-8})$alkyl; $(C_{1-6})$alkylcarbonyl; di-$(C_{1-6})$alkylaminocarbonyl; $(C_{3-8})$cycloalkylcarbonyl; benzyl; benzoyl; $(C_{1-6})$alkyloxycarbonyl; aralkyloxycarbonyl, pyridine; pyrimidine; phenyl; phenyl substituted thiazole ring; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; $R_x$ is hydrogen; alkyl; cycloalkyl; alkenyl, cycloalkylalkyl, aryl, aralkyl, heterocyclyl, or heterocyclylalkyl, each optionally mono- or independently di-substituted with $R^{12}$; $R_y$ is absent or is halogen, $(C_{1-8})$alkyl, $(C_{1-8})$alkoxy, O-alkylcarboxylate, O-aralkylcarboxylate, N-alkylcarboxamido, N-aralkylcarboxamido; or phenyl; s is 1 to 6; t is 0 to 6; and u is 0 to 3.

20. The method of claim 18 wherein $R^1$ is a group of the formula:

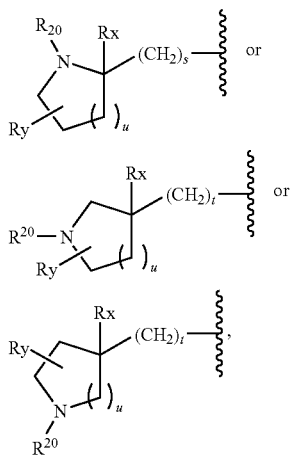

where $R^{20}$ is an N-protecting group or is $(C_{1-8})$alkyl; $(C_{1-6})$alkylcarbonyl; di-$(C_{1-6})$alkylaminocarbonyl; $(C_{3-8})$cycloalkylcarbonyl; benzyl; benzoyl; $(C_{1-6})$alkyloxycarbonyl; aralkyloxycarbonyl, pyridine; pyrimidine; phenyl; phenyl substituted thiazole ring; phenylaminocarbonyl; alkylsulfonyl; or phenylsulfonyl; where the benzyl, benzoyl, pyridine, pyrimidine, phenyl, phenylaminocarbonyl, alkylsulfonyl, and phenylsulfonyl groups are optionally mono- or independently di-substituted with $R^{12}$; $R_x$ is hydrogen; alkyl; cycloalkyl; alkenyl, cycloalkylalkyl, aryl, aralkyl, heterocyclyl, or heterocyclylalkyl, each optionally mono- or independently di-substituted with $R^{12}$; $R_y$ is absent or is halogen, $(C_{1-8})$alkyl, $(C_{1-8})$alkoxy, O-alkylcarboxylate, O-aralkylcarboxylate, N-alkylcarboxamido, N-aralkylcarboxamido; or phenyl; s is 1 to 6; t is 0 to 6; and u is 0 to 3.

21. The method of claim 20, wherein $R^{20}$ is benzyl, Cbz, Boc, Fmoc, Alloc, Teoc, acetyl, pivaloyl, benzoyl, cyclohexylcarbonyl, or phenylsulfonyl.

22. The method of claim 20 wherein u is 1 or 2.

23. The method of claim 20 wherein t is 0 or 1.

24. The method of claim 20 wherein $R_x$ is hydrogen, methyl, trifluoromethyl, ethyl, pentafluoroethyl, propyl, butyl, phenyl or benzyl, wherein the phenyl and benzyl are optionally perfluorinated or substituted with 1, 2 or 3 groups independently selected from F, Cl, Br, I, R', OR', CN, SH, $NO_2$, $NR'_2$, COOR', $CF_3$, $OCF_3$, SR', S(O)R', or S(O)$_2$R', wherein R' is H or $C_{1-4}$ alkyl optionally substituted with one or more groups consisting of F and Cl.

25. The method of claim 20, wherein $R_y$ is absent.

26. The method of claim 18 wherein $R^1$ is
cycloalkyl; cycloalkylalkyl; bicycloalkyl; tricycloalkyl; alkylcycloalkyl; hydroxyalkylcycloalkyl; hydroxycycloalkyl; hydroxybicycloalkyl; hydroxytricycloalkyl; bicycloalkylalkyl; alkylbicycloalkyl; cycloalkenyl; aryl, heteroaryl; heteroarylalkyl; cycloheteroalkyl or cycloheteroalkylalkyl; all optionally mono- or independently plurisubstituted with halogen, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylamino-carbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfinyl, aminosulfonyl, alkylsulfinyl, sulfonamido or sulfonyl.

27. The method of any of claim 1 or 2 wherein $R^2$ and $R^3$ are independently hydroxy, methoxy, ethoxy, n-propoxy, i-propoxy, or n-butoxy; or together are 1,2-dioxaethylene, 1,3-dioxapropylene, 2,3-dimethyl-2,3-dioxabutane, or pinanedioxy.

28. The method of any of claim 1 or 2 wherein the coupling is conducted in the presence of solvent.

29. The method of claim 28 wherein the solvent is water, tetrahydrofuran, 2-methyltetrahydrofuran, dichloromethane, dimethylformamide, or a mixture of any two or more thereof.

30. The method of claim 1 or 2 further comprising removing $Pr^1$ at each occurrence.

31. The method of claim 30 wherein $Pr^1$ is at each occurrence Cbz and is removed by hydrogenolysis.

32. The method of claim 30 wherein $Pr^1$ is at each occurrence Boc and are removed by acidolysis.

33. The method of claim 30 further comprising hydrolyzing $R^2$ and $R^3$ to hydroxyls.

34. The method of claim 1 or 2 further comprising hydrolyzing $R^2$ and $R^3$ to hydroxyls.

35. The method of claim 34 wherein the hydrolysis is carried out in the presence of phenyl boronic acid, water, and an ether.

36. The method of claim 35 wherein the ether is tertbutylmethylether, 2-methyltetrahydrofuran, or a mixture thereof.

37. The method of claim 20 wherein $R^1$ is

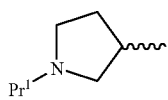

wherein the squiggle line indicates an R or S configuration or combination thereof.

38. The method of claim 1 wherein the compound of formula I is a compound of formula:

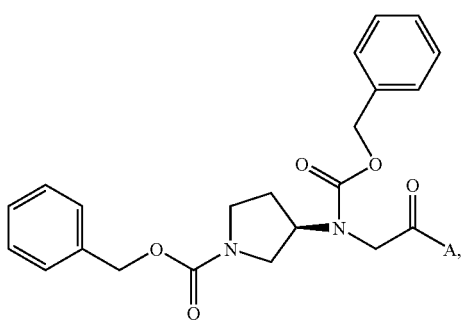

wherein A is as defined in claim 1;
the compound of formula II is a compound of formula:

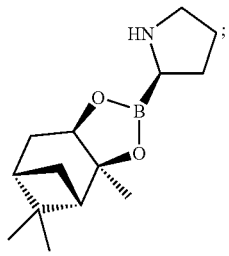

and
the compound of formula III is a compound of formula

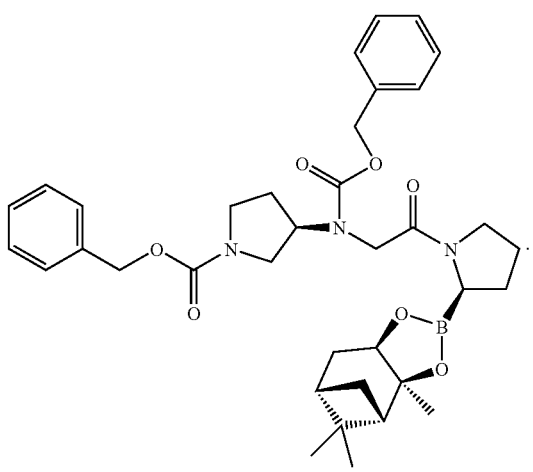

39. The method of claim 38, wherein A is OC(O)OR, wherein R is substituted or unsubstituted $C_{1-8}$ alkyl.

40. The method of claim 39, wherein R is ethyl, isopropyl, or isobutyl.

41. The method of claim 30 further comprising hydrolyzing $R^2$ and $R^3$ to hydroxyls to form a compound of the formula

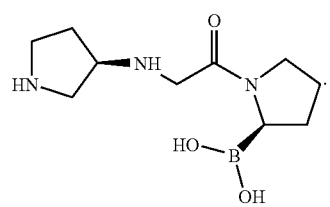

* * * * *

UNITED STATES PATENT AND TRADEMARK OFFICE
CERTIFICATE OF CORRECTION

PATENT NO. : 7,786,312 B2  
APPLICATION NO. : 11/996792  
DATED : August 31, 2010  
INVENTOR(S) : David A. Campbell et al.

Page 1 of 1

It is certified that error appears in the above-identified patent and that said Letters Patent is hereby corrected as shown below:

In column 1, line 38, delete "heterocylic" and insert -- heterocyclic --, therefor.

In column 4, line 5, delete "($C_{2-2}$)alkynyl;" and insert -- ($C_{2-12}$)alkynyl; --, therefor.

In column 12, line 66, delete "hydroxy"" and insert -- hydroxyl" --, therefor.

In column 13, line 12, delete "(S,S,)" and insert -- (S,S) --, therefor.

In column 13, line 13, delete "dimethyoxy" and insert -- dimethoxy --, therefor.

In column 14, line 9, delete "hydroxyamines" and insert -- hydroxyimines --, therefor.

In column 15, line 26, delete "xanthenyl," and insert -- xanthinyl, --, therefor.

In column 15, line 27, delete "guanidyl," and insert -- guaninyl, --, therefor.

In column 15, line 43, delete "xanthenyl," and insert -- xanthinyl, --, therefor.

In column 15, line 43, delete "guanidyl," and insert -- guaninyl, --, therefor.

In column 16, line 35, delete "10,1,1" and insert -- 10,11 --, therefor.

In column 20, line 5, delete "12)" and insert -- $I_2$) --, therefor.

In column 27, line 64, in Claim 18, before "heteroaryl;" delete "aralkyl;".

In column 28, line 28, in Claim 19, delete "pyridinyl," and insert -- pyridinyl --, therefor.

Signed and Sealed this

Twenty-first Day of December, 2010

David J. Kappos  
*Director of the United States Patent and Trademark Office*